United States Patent
Ishii et al.

(10) Patent No.: US 8,123,496 B2
(45) Date of Patent: Feb. 28, 2012

(54) TWO-UNIT PUMP FOR LIQUID CHROMATOGRAPH WITH FLOW SENSOR ARRANGEMENT

(75) Inventors: Kimihiko Ishii, Hitachinaka (JP);
Kiyotoshi Mori, Hitachinaka (JP);
Masahito Ito, Hitachinaka (JP);
Hironori Kaji, Hitachinaka (JP);
Takefumi Yokokura, Kasama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/845,487

(22) Filed: Jul. 28, 2010

(65) Prior Publication Data
US 2010/0288027 A1 Nov. 18, 2010

Related U.S. Application Data

(62) Division of application No. 11/582,455, filed on Oct. 18, 2006, now abandoned.

(30) Foreign Application Priority Data

Oct. 19, 2005 (JP) .................................. 2005-303939

(51) Int. Cl.
*F04B 1/06* (2006.01)
*F04B 49/20* (2006.01)
*B01D 15/10* (2006.01)

(52) U.S. Cl. ........................ 417/254; 210/198.2; 417/20

(58) Field of Classification Search ................ 417/2, 20, 417/244, 254; 73/61.52, 61.56; 210/198.2; 137/554
See application file for complete search history.

(56) References Cited

U.S. PATENT DOCUMENTS

| 4,422,942 A | 12/1983 | Allington |
| 4,808,077 A * | 2/1989 | Kan et al. ........................... 417/2 |
| 4,810,168 A * | 3/1989 | Nogami et al. .................... 417/2 |
| 4,883,409 A * | 11/1989 | Strohmeier et al. ............. 417/43 |
| 4,919,595 A * | 4/1990 | Likuski et al. ................... 417/18 |

(Continued)

FOREIGN PATENT DOCUMENTS

JP 55-128678 10/1980

(Continued)

*Primary Examiner* — Devon C Kramer
*Assistant Examiner* — Nathan Zollinger
(74) *Attorney, Agent, or Firm* — McDermott Will & Emery LLP0

(57) ABSTRACT

A pump device which accurately detects a flow rate of a pump, performs real-time control of the flow rate, and thus can suppress a flow rate error caused by occurrence of pulsation. Control of a pump rotation speed by a pressure sensor has low responsiveness in a low pressure region, and a correlation between a pressure and a flow rate is incomplete in a high flow rate region. With this taken into consideration, a flow rate sensor is disposed at an outlet port of a second pump. A position detection sensor detects a point where a first pump is shifted from a suction mode to a discharge mode. Moreover, the flow rate sensor detects that there is no discharge from the pump, and that there is discharge from the pump alone. Accordingly, a controller sets a rotation speed of a motor to a speed double the previous speed (double the normal rotation speed). When the flow rate sensor detects an increase in the flow rate at the outlet port of the second pump, the controller returns the rotation speed of the motor to a normal rotation speed. The rotation speed of the motor is controlled by accurate flow rate detection by the flow rate sensor. Thus, occurrence of pulsation can be suppressed.

2 Claims, 9 Drawing Sheets

U.S. PATENT DOCUMENTS

| | | | |
|---|---|---|---|
| 5,108,264 A * | 4/1992 | Abdel-Rahman | 417/20 |
| 5,664,937 A * | 9/1997 | Takahashi et al. | 417/22 |
| 5,852,231 A * | 12/1998 | Kaji | 73/61.56 |
| 6,712,587 B2 * | 3/2004 | Gerhardt et al. | 417/390 |
| 7,189,320 B2 * | 3/2007 | Takao et al. | 210/198.2 |
| 7,588,423 B2 * | 9/2009 | Takao et al. | 417/254 |
| 2004/0164013 A1 * | 8/2004 | Takao et al. | 210/198.2 |
| 2005/0084386 A1 * | 4/2005 | Mori et al. | 417/199.1 |

FOREIGN PATENT DOCUMENTS

| | | |
|---|---|---|
| JP | 02147953 A | 6/1990 |
| JP | 8-15245 | 1/1996 |
| JP | 2564588 | 10/1996 |
| JP | 2604362 | 1/1997 |
| JP | 11-50967 | 2/1999 |
| WO | WO 2005/050190 A2 | 6/2005 |
| WO | WO 2005050190 A2 * | 6/2005 |

* cited by examiner

TWO-UNIT PUMP FOR LIQUID CHROMATOGRAPH WITH FLOW SENSOR ARRANGEMENT

CROSS-REFERENCE TO RELATED APPLICATIONS

This application is a Divisional of U.S. application Ser. No. 11/582,455, filed on Oct. 18, 2006 now abandoned, claiming priority of Japanese Patent Application No. 2005-303939, filed on Oct. 19, 2005, the entire contents of each of which are hereby incorporated by reference.

BACKGROUND OF THE INVENTION

1. Field of the Invention

The present invention relates to a pump for feeding a solvent, and more particularly to a pump for a liquid chromatograph device, which is accurate without any fluctuations in a flow rate in a wide flow range and a wide pressure range.

2. Description of the Related Art

In liquid chromatographic analysis, a sample to be analyzed is introduced into a separation column filled with filler particles having specific particle size and composition, and a single solvent or a mixture of a plurality of solvents is fed into the separation column by a pump. The sample introduced into the separation column is eluted for each component based on its chemical properties and composition, and the component is detected by a detector.

It is preferable that a solvent feed pump for liquid chromatograph can continuously feed a solvent at an accurate flow rate and in a stable state with few fluctuations in the flow rate under high pressure and in a wide flow range. Moreover, it is preferable that the solvent feed pump can mix a plurality of solvents and can perform a gradient operation of changing a mixture ratio of the solvents with time. Furthermore, the solvent feed pump is required to accurately and precisely control also a composition of the mixed solvents.

A variation in the flow rate of the solvents passing through the separation column or in the composition of the mixed solvents varies retention time of each component peak or peak height and area of each component on a chromatogram to be detected. The peak retention time is basic qualitative information, which takes a value unique to the component separated by the liquid chromatograph. The peak height and area indicate a concentration of the component separated by the liquid chromatograph. Therefore, the variation in the flow rate or in the composition of the mixed solvents causes uncertainty in peak identification. As a result, accuracy of quantitative measurement and reproducibility are impaired.

As a feed pump for continuous feeding, which is suitable for the liquid chromatograph, a dual piston pump is widely known, which includes a reciprocating piston in each of two pump heads connected to each other and uses one motor to drive a common camshaft designed to allow the piston to have predetermined phase difference and a predetermined stroke.

According to the technology described in Japanese Unexamined Patent Publication 55-128678 (1980), a cam designed to set the same amount of liquid flow at every point in a rotation cycle of a camshaft is used. Moreover, a pressure fluctuation is monitored by a pressure sensor installed inside a pump. In a case where the pressure is lowered at the start of discharge by a first piston, a rotational speed of a motor is increased by a certain multiplying factor to compress a solvent. Thus, a pulsating flow with diminished pulsing is realized by real-time control.

A control method using a pressure sensor described in Japanese Unexamined Patent Publication 55-128678 (1980) is a method realized on an assumption that a flow rate and the pressure are totally correlated with each other. For pressure measurement, there are pressure sensors having various principles. However, there are restrictions placed on the sensor, such as that the sensor has high fastness, reliability and stability even when used under high pressure for a long period of time, which are required of the liquid chromatograph, that the sensor has excellent corrosion resistance to various solvents such as an organic solvent, an acid solvent and an alkali solvent, that the sensor is small enough to be installed inside a device, that a detection part has a small solvent contact capacity, and that the sensor is excellent in responsiveness. Thus, as a typical pressure sensor, a semiconductor strain gauge pressure transducer is widely used, which converts a pressure into displacement through a diaphragm made of a stainless member or the like having excellent corrosion resistance, and takes out the displacement in the form of an electrical quantity by a bridge circuit.

However, even the pressure sensor described above requires response time of several hundred milliseconds under low pressure. Thus, the pressure sensor is insufficient for real-time control of a piston, which is required to operate at high speed. Therefore, Japanese Patent Publication No. 2604362 and Japanese Patent Publication No. 2564588 disclose pumps having a learning function for sequentially changing the number of revolutions and a phase of a motor for each period in a direction of reducing a pressure fluctuation by referring to a pressure profile of the previous period. However, such a pump has a drawback that the pump is vulnerable to such changes as a change in a flow rate and inclusion of bubbles.

The conventional technologies described above are all attempts to obtain a constant flow rate by constant control of the pressure fluctuation. In hydrodynamics, the Hagen-Poiseuille equation is known, which indicates that a flow rate and a pressure difference are proportional to each other, as a property of a flow inside a sufficiently developed straight circular tube.

However, as to an actual passage of liquid chromatograph, movements of a stirring member inside the passage and of a piston are added inside the passage to a configuration including various sizes and shapes of tubes, joints, blocks and the like. Accordingly, turbulent flows and vortexes are generated everywhere. Therefore, it is very difficult to accurately calculate correlation between the flow rate and the pressure.

Particularly, when the flow rate is increased, and turbulent flows are generated, the Hagen-Poiseuille equation by itself may not be sufficient to obtain a correlation between the pressure and flow rate. It is, therefore, virtually impossible to obtain a correlation between the pressure and the flow rate. Even if a composition and a temperature of a solvent are constant, a pressure difference inside the passage is sequentially changed by minute clogging and the like, and a detected pressure also fluctuates with time. Because of this, a minute leak from the joint and a seal part, which are provided inside the passage, cannot be eliminated. Consequently, it is very risky to discuss an absolute value of the flow rate based on an absolute value of the detected pressure.

In a case of a pump which has more than one pair of the foregoing dual piston pump units connected thereto and can perform a gradient operation of changing a mixture ratio of a plurality of solvents with time, accuracy and uniformity of a solvent composition to be synthesized become a key factor that determines performance of the liquid chromatograph.

Accordingly, the pump units are required to have stricter flow rate accuracy and flow rate precision in a wide flow rate range.

Specifically, in such a pump which performs a high-pressure gradient operation, it is known that a minute flow rate error or flow rate fluctuation in each pump unit makes it difficult to feed the solvent while maintaining stable accuracy and uniformity of the solvent composition to be synthesized.

For example, Japanese Unexamined Patent Publication 8-15245 (1996) and 11-50967 (1999) disclose a gradient controller which predicts time when stable feeding would be disturbed by pressure interference between pumps, based on parameters determined by a set flow rate and a trial, and would perform feeding according to a pattern in a stable state without the interference during the predicted time.

However, in a case where flow rates in the respective pumps constantly vary, the time when the above disturbance in feeding (pressure fluctuation) would occur differs between the respective pumps. Therefore, it is difficult to accurately predict the period of time when the pressure interference would occur.

Therefore, a pump capable of feeding a solvent at a stable solvent mixture ratio is conceivable. Specifically, the pump has pressure sensors provided in a first pump chamber and in a passage after a second pump chamber. Moreover, the pump compresses the solvent by controlling pistons so as to set a pressure difference between the both pressure sensors to have a constant value, and corrects a pressure drop at a time when the inside of the first pump chamber is connected to the second pump chamber.

However, as described above, in the control by the pressure sensors, a problem with responsiveness of the pressure sensors in a low pressure region causes an uncontrollable error due to an incomplete correlation between the pressure and the flow rate in a high flow rate region. As a result, accuracy and precision of the solvent mixture ratio are impaired.

Moreover, the methods described above have a critical flaw as described below. A control error is caused by that zero points of both pressure sensors do not completely coincide with each other, and linear characteristics thereof do not, either. Since the control error is unavoidable, it is difficult to equally eliminate pressure fluctuations (flow rate fluctuations) over a wide flow rate range.

SUMMARY OF THE INVENTION

It is an object of the present invention to provide a pump device which accurately detects a flow rate of a pump, performs real-time control of the flow rate, and thus can suppress a flow rate error caused by occurrence of pulsation.

A pump device of the present invention includes: a first piston which moves back and forth in a first pump chamber; a second piston which moves back and forth in a second pump chamber; a connecting pipe which connects an outlet port of the first pump chamber to an inlet port of the second pump chamber; an inlet side valve which is connected to an inlet port of the first pump chamber, and switches a flow of a fluid into and out of the first pump chamber; an outlet side valve which is connected to the connecting pipe, and switches the flow of the fluid into and out of the second pump chamber from the first pump chamber through the connecting pipe; and piston driving means for moving the first and second pistons back and forth.

The pump device of the present invention further includes: a position detection sensor which detects a back-and-forth movement position of the first piston; a flow rate sensor which detects a flow rate of the fluid flowing out of the outlet port of the second pump chamber; and control means for controlling a speed of driving the first and second pistons by the piston driving means, based on the back-and-forth movement position of the first piston, which is detected by the position detection sensor, and the flow rate of the fluid flowing out of the outlet port of the second pump chamber, which is detected by the flow rate sensor.

Moreover, a method for driving a pump device of the present invention includes the steps of: detecting a first region where the fluid flows into the first pump chamber from the inlet port and the fluid flows out of the outlet port of the second pump chamber; moving the first and second pistons at a first driving speed in the first region; detecting a start point of a second region where the first pump chamber is shifted from a fluid suction mode to a discharge mode; moving the first and second pistons at a second driving speed that is a speed double the first driving speed when the second region is detected and it is detected from the flow rate of the fluid flowing out of the outlet port of the second pump chamber that no fluid flows out of the first pump chamber and the fluid only flows out of the second pump chamber; and returning the speed of driving the first and second pistons to the first driving speed upon detection of an increase in an amount of the fluid flowing out of the second pump chamber.

Furthermore, in the pump device and the method for driving a pump device according to the present invention, the control means detects a first region where the fluid flows into the first pump chamber from the inlet port and the fluid flows out of the outlet port of the second pump chamber, moves the first and second pistons at a first driving speed in the first region, detects a start point of a second region where the first pump chamber is shifted from a fluid suction mode to a discharge mode, moves the first and second pistons at a second driving speed that is a speed double the first driving speed when the second region is detected and it is detected from the flow rate of the fluid that no fluid flows out of the first pump chamber and the fluid only flows out of the second pump chamber, and returns the speed of driving the first and second pistons to the first driving speed when the flow rate sensor detects an increase in an amount of the fluid flowing out of the second pump chamber.

Moreover, the pump device and the method for driving a pump device according to the present invention further include a second flow rate sensor which is connected to the connecting pipe and detects a flow rate of the fluid flowing inside the connecting pipe, and the speed of driving the first and second pistons is returned to the first driving speed when it is detected from the flow rate detected by the second flow rate sensor that the outlet valve is shifted from a closed state to an opened state.

Moreover, the pump device and the method for driving a pump device according to the present invention further include an opening and closing detection sensor which detects opened and closed states of the outlet side valve, and the speed of driving the first and second pistons is returned to the first driving speed when the opening and closing detection sensor detects that the outlet valve is shifted from the closed state to the opened state.

According to the present invention, it is possible to realize a pump device which accurately detects a flow rate of a pump, performs real-time control of the flow rate, and thus can suppress a flow rate error caused by occurrence of pulsation, and to realize a method for driving the pump device.

According to the present invention, a solvent can be continuously fed at an accurate flow rate and in a stable state with few flow rate fluctuations (pulsating flows). Moreover, also in a gradient operation of changing a mixture ratio of solvents with time, a composition of the mixed solvents can also be accurately and precisely controlled.

DETAILED DESCRIPTION OF THE PREFERRED EMBODIMENTS

With reference to the accompanying drawings, the foregoing and other embodiments of the present invention will be described below.

Figure 1:
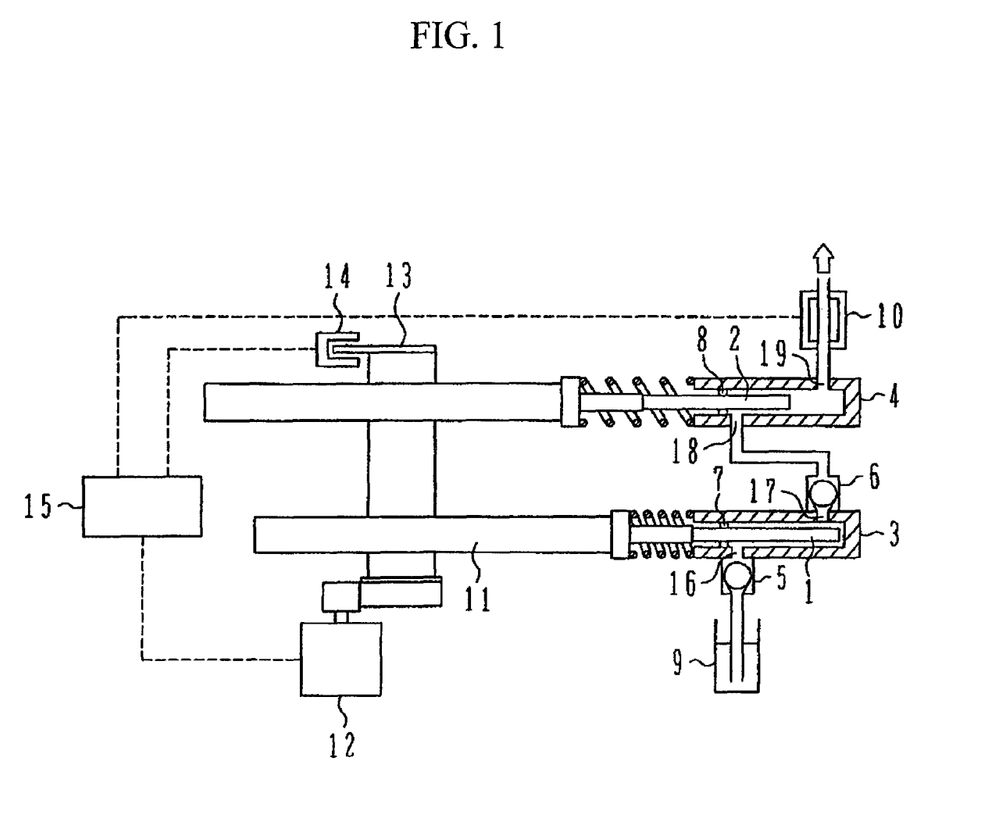
FIG. 1 is a schematic configuration diagram of a pump device using a flow rate sensor according to a first embodiment of the present invention.

FIG. 1 is a schematic configuration diagram of a pump unit (pump device) using a flow rate sensor according to a first embodiment of the present invention.

In FIG. 1, the pump unit includes a first pump chamber 3 and a second pump chamber 4. A first piston 1 and a second piston 2 are disposed in the respective pump chambers 3 and 4 with seal members 7 and 8. The first and second pistons 1 and 2 are moved back and forth by rotation of a cam 11. In accordance with the back-and-forth movement of the pistons, inlet side valve 5 connected to inlet port 16 and outlet side valve 6 connected to inlet port 18 and outlet port 17 for checking a backflow are opened and closed. A mobile phase 9 is delivered toward an outlet of the second pump chamber 4 from the pump chamber 3 through the pump chamber 4 by the operations of the pistons 1 and 2 and the valves 5 and 6.

A flow rate sensor 10 is provided in the outlet of the second pump chamber 4, and detected flow rates are sequentially introduced into a controller 15. The cam 11 is rotated by a motor 12 disposed on one end of its shaft, and the motor 12 is controlled by the controller 15 including a computer.

A detection plate 13 and a position detection sensor 14 are provided on the other end of the shaft of the cam 11, and an angular position of the camshaft, which is detected by the position detection sensor 14, is introduced into the controller 15. In the first embodiment of the present invention, as the inlet side and outlet side valves 5 and 6 for checking the backflow, passive check valves are used. However, active solenoid valves or rotary lapped valves can also be used. Moreover, it is also possible to detect a pressure simultaneously with the flow rate by providing a pressure sensor (not shown) in an outlet port 19 of the second pump chamber 4.

Figure 2:
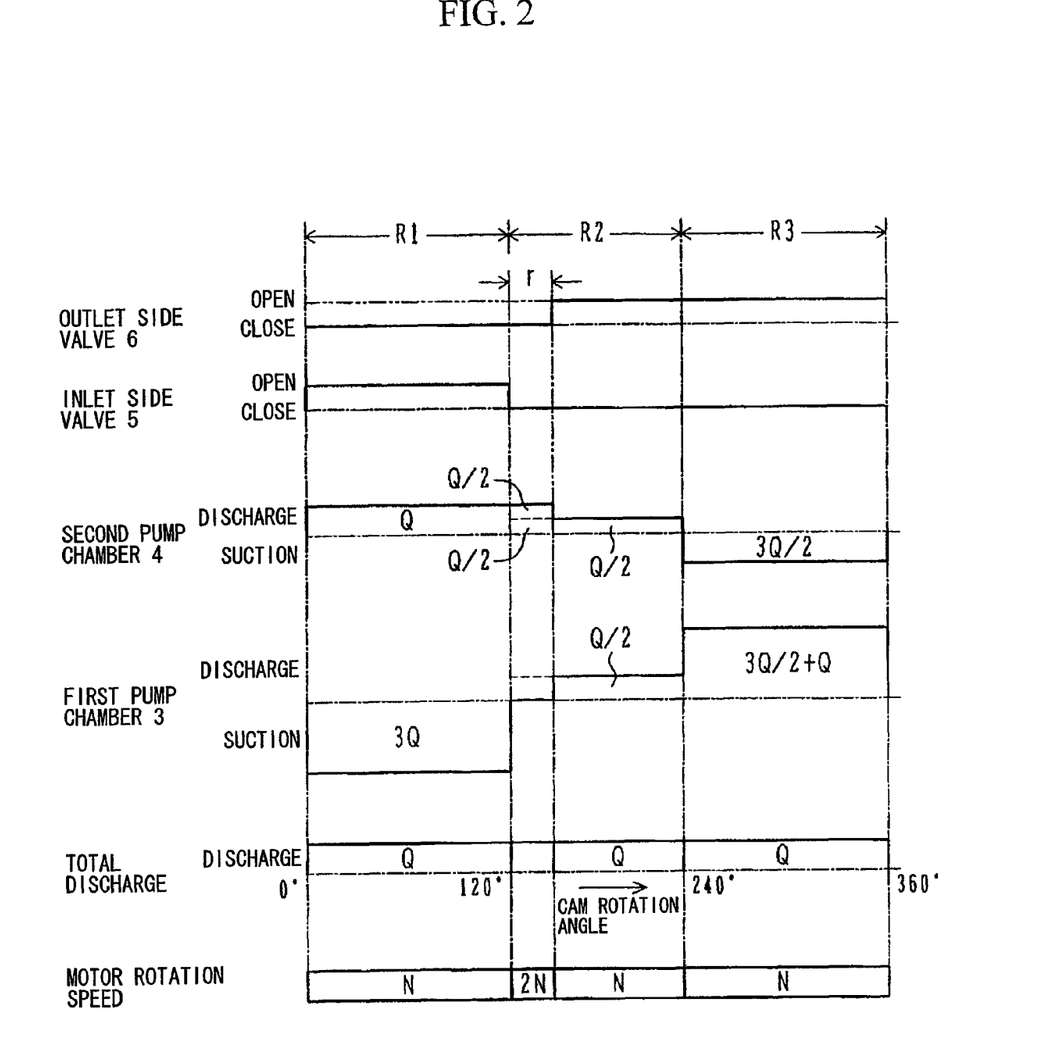
FIG. 2 is a view showing an example of a flow rate control cycle of the pump device using the flow rate sensor according to the first embodiment of the present invention.

FIG. 2 is an explanatory view showing an example of a flow rate control cycle by use of the pump unit according to the first embodiment of the present invention.

In FIG. 2, one cycle of the pump unit is divided into three regions R1 to R3 corresponding to a shape of the cam 11. In the region R1, the first pump chamber 3 is in a suction mode (a suction amount is 3Q per unit time), and the second pump chamber 4 is in a discharge mode (a discharge amount is Q per unit time).

Moreover, in the region R2, both of the first and second pump chambers 3 and 4 are in the discharge mode (each discharge amount is Q/2 per unit time). In the region R3, the motor 12 is rotated at a certain rotation speed (the number of revolutions N per unit time) so as to operate the first pump chamber 3 in the discharge mode (a discharge amount is (3Q/2)+Q per unit time) and to operate the second pump chamber 4 in the suction mode (a suction amount is 3Q/2 per unit time).

When the pump chambers are operated as described above, the inlet side valve 5 is opened and the outlet side valve 6 is closed in the region R1, and the inlet side valve 5 is closed and the outlet side valve 6 is opened in the regions R2 and R3. The number of revolutions N of the motor 12 is a value calculated based on a set flow rate Q' and a designed value of the discharge amount per one cycle of the pump unit. The number of revolutions N is preferably a value corrected based on a deviation between a flow rate q, which is detected by the flow rate sensor 10 in stable feeding after the operation is started, and the set flow rate Q'.

In a case where the outlet side of the second pump chamber 4 is under high pressure (for example, 20 MPa), when the first pump chamber 3 is switched from the suction mode to the discharge mode, the outlet side valve 6 is not opened in the beginning (in other words, in a region r at the beginning of the region R2). This is because the high pressure described above is applied to the outlet side valve 6 by using the mobile phase 9 as a medium. Moreover, the region r varies with a compression rate of the mobile phase to be used.

Therefore, in the region r, there is no discharge by the first pump chamber 3 and there is discharge only by the second pump chamber 4. Accordingly, the total discharge amount is reduced to half, and a pulsating flow is caused in a period over the regions R1, r and R2.

The following measures are normally taken to solve the problem described above.

First, a position where the first pump chamber 3 is switched from the suction mode to the discharge mode is detected. The position can be detected by detecting a bottom dead center position of the first piston 1 by use of the position detector 14. Moreover, when there is no discharge by the first pump chamber 3 and there is only discharge by the second pump chamber 4, the flow rate in the outlet of the pump chamber 4 is lowered. Thus, this drop in the flow rate is detected by the flow rate sensor 10.

The rotation speed of the motor 12 is doubled only when both of a position detection signal and a flow rate drop detection signal are detected (AND condition). Specifically, the number of revolutions per unit time is set to 2N. Thus, the mobile phase is fed by the second pump chamber 4 at the doubled flow rate so as to compensate for the amount not discharged by the first pump chamber 3.

Next, when the outlet side valve 6 is opened, the flow rate from the outlet port 19 of the second pump chamber 4 is increased. Thus, this increase in the flow rate is detected by the flow rate sensor 10. Since the discharge is performed also by the first pump chamber 3, the rotation of the motor 12 is returned from the double speed rotation to the rotation at a speed half the double speed, in other words, to the original number of revolutions N, based on a flow rate increase signal detected.

As described above, in the regions R1 and R3, rotation speed priority control is performed. Meanwhile, in the region R2, when the rotation speed is switched according to the flow rate, the switch prevents a change in the flow rate, which would be caused by compression of the mobile phase 9 at a time when the first pump chamber 3 is shifted from the suction mode to the discharge mode. As a result, it is possible to perform feeding at a constant flow rate (Q) without pulsating.

Specifically, real-time control of the flow rate is performed by using the flow rate sensor 10 included inside the pump unit. Thus, compared with the conventional control using pressure sensors, control responsiveness is improved in a low pressure region. Moreover, in a high flow rate region, control errors caused by a flow state variation can be reduced. Thus, flow rate fluctuations (pulsating flows) can be reduced.

Furthermore, control of the number of revolutions of the motor 12 based on the measured flow rate makes it possible to obtain an accurate flow rate even if a minute leak from a joint or a seal part occurs or even if a state inside a passage changes over time.

Thus, mechanical differences between the pump devices can be reduced. Note that, by simultaneously providing a pressure sensor in FIG. 1, a data correlation between the system of the present invention and a conventional system and correlation between the flow rate and the pressure can also be checked. Moreover, occurrence of a clogging in a pipe can also be detected by the pressure sensor.

Moreover, as another example of the flow rate control cycle, the number of revolutions N of the motor 12 may be controlled over the entire sections of the cam 11 so as to set the flow rate detected by the flow rate sensor 10 to be always constant without dividing one cycle into the three regions R1 to R3 described above.

Figure 3:
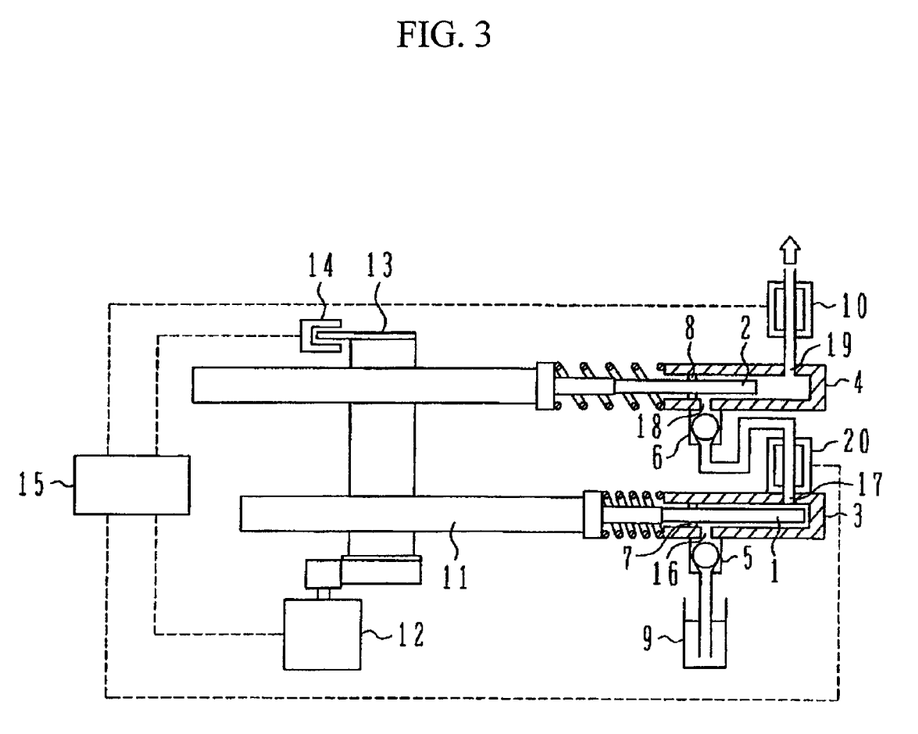
FIG. 3 is a schematic configuration diagram of a pump device using a flow rate sensor according to a second embodiment of the present invention.

FIG. 3 is a schematic configuration diagram of a single pump unit (pump device) using a flow rate sensor according to a second embodiment of the present invention.

A structural different between the second embodiment of the present invention and the first embodiment shown in FIG. 1 is that a second flow rate sensor 20 is disposed between an outlet port 17 of the first pump chamber and the outlet side valve 6.

In a flow rate control cycle of the pump unit shown in FIG. 2, a point where flow rate fluctuations (pulsating flows) are most likely to occur is an end point of a region r in which the motor 12 is operated at double speed. Specifically, accurately determining the time when the outlet side valve 6 is opened and immediately returning the double-speed operation of the motor 12 to the original operation with the reference number of revolutions N are the most important keys to reducing the flow rate fluctuations.

By use of the configuration according to the second embodiment of the present invention shown in FIG. 3, the moment at which the outlet side valve 6 is opened can be more accurately detected by the flow rate sensor 20. Thus, compared with the configuration shown in FIG. 1, the flow rate fluctuations can be further reduced in the second embodiment shown in FIG. 3. Particularly, the importance of the second embodiment is further demonstrated in an embodiment of a high-pressure gradient pump system to be described later.

Moreover, in order to realize a cheap pump device, the motor may be operated at a motor rotation speed calculated based on a set flow rate Q' and a designed value of a discharge amount per one cycle of the pump unit, while omitting the flow rate sensor 10 from the configuration shown in FIG. 3. In this case, although reliability for accuracy of the flow rate is lowered, stable feeding without flow rate fluctuations can be performed.

Figure 4:
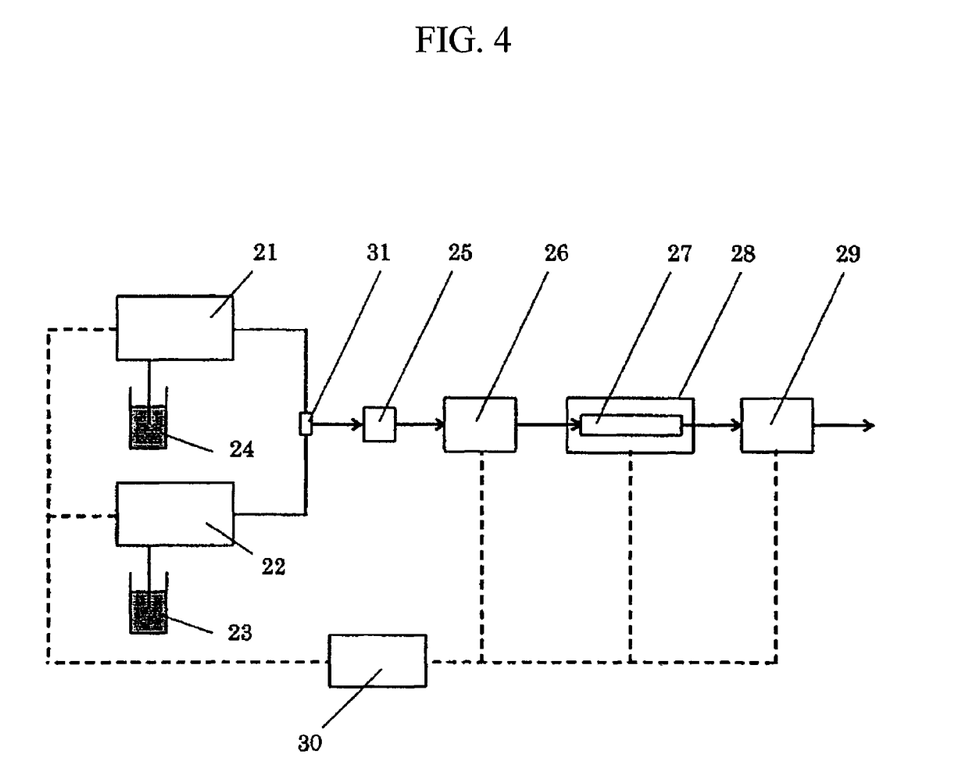
FIG. 4 is a schematic configuration diagram showing a high-pressure gradient pump system including two pump devices of the present invention, and liquid chromatograph including the high-pressure gradient pump system.

FIG. 4 is a schematic configuration diagram showing a high-pressure gradient pump system formed by using two pump units according to the first or second embodiment of the present invention, and showing liquid chromatograph including the high-pressure gradient pump system.

In FIG. 4, mobile phases 23 and 24 are fed by pump units 21 and 22 while changing flow rates thereof with time, and are combined at a T connecting pipe 31. The combined mobile phases 23 and 24 are stirred with each other by a mixer 25. Thereafter, a sample to be analyzed is added to the mobile phases 23 and 24 by an injector inside an autosampler 26.

The mobile phases 23 and 24 having the sample added therein by the autosampler 26 are introduced into a separation column 27. In order to perform multicomponent separation with good reproducibility, the separation column 27 is installed inside a column oven 28 kept at a constant temperature. The respective components separated by the separation column 27 are detected by a detector 29, and data concerning the components is processed and saved by a data processor 30. Moreover, in this embodiment, the data processor 30 also controls operations of the respective parts 21, 22 and 25 to 29.

As described in the foregoing Patent Document 5, in high-pressure gradient liquid chromatograph, when double-speed control regions of the respective pump units 21 and 22 overlap with each other, there occurs a phenomenon that a mixture ratio of eluents is changed by pressure interference between the pumps.

Specifically, when double-speed rotation of one of the pump units 21 and 22 is terminated while the double-speed rotation of the other pump unit is performed, an output side pressure of the pump unit having its rotation terminated is increased. Thus, the pump unit in the double-speed rotation is also stopped at the time when the pressure is increased, in accordance with the pressure increase in the pump unit having its double-speed rotation terminated.

Since the above stopping of the rotation of the pump unit is performed earlier than an original stop point, the pressure at the output side of the pump is increased by the opening of the input side valve. Accordingly, an output flow rate is reduced to half until a point at which discharge is started by the both pump units. Thus, there arises a problem that the mixture ratio is changed.

In order to solve the problem described above, it is conceivable to perform feeding at a stable solvent mixture ratio by providing pressure sensors in the first pump chamber and in the passage after the second pump chamber, compressing solvents by controlling the piston so as to set a pressure difference between both pressure sensors to be a constant value, and correcting a pressure drop when the inside of the first pump chamber is connected with the second pump chamber.

Figure 5:
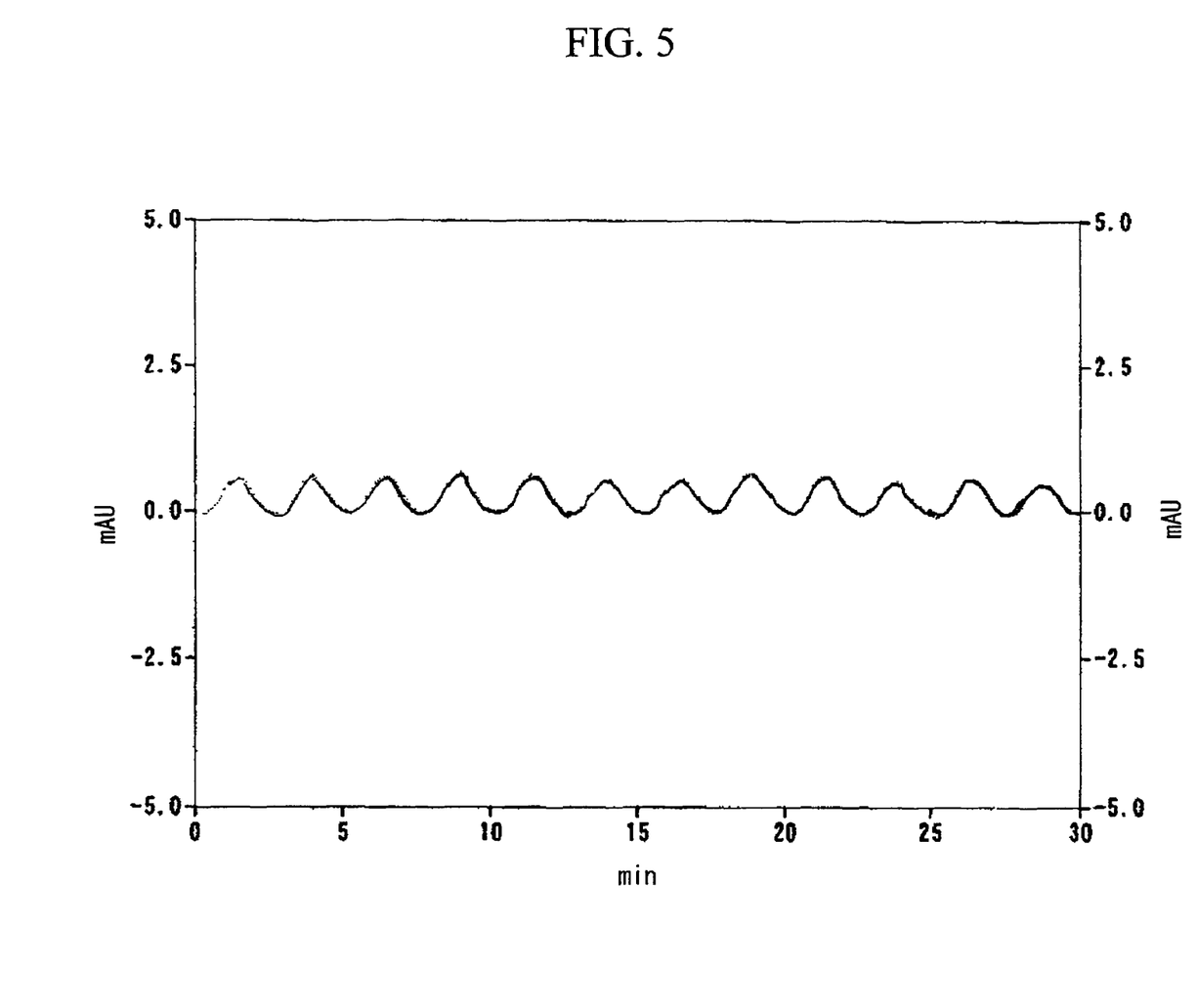
FIG. 5 is a view showing a measurement result in high-pressure gradient liquid chromatograph using a pump device having a configuration different from that of the present invention.

FIG. 5 is a view showing a result of measurement performed by using a UV absorbance detector as the detector 29 in high-pressure gradient liquid chromatograph using two pressure sensors unlike the present invention. The pressure sensors are to correct a pressure drop at the time when inside of the first pump chamber is communicated with the second pump chamber as described above.

The result shown in FIG. 5 is a base line of a chromatogram obtained in the following manner. Specifically, by using water as the mobile phase 23 and a 20 ppm caffeine solution as the mobile phase 24, the mobile phases are fed by the pump units 21 and 22 at a combined flow rate of 200 μl/min with a mixture ratio of the mobile phases 23 and 24 set to 95:5. Then, absorbance in a measurement wavelength of 273 nm is detected.

A discharge amount per one cycle of the pump units 21 and 22 is 25 μl. Moreover, a periodic ripple is observed, which is synchronized with a flow rate control cycle 2.5 min of the pump unit having the mixture ratio of 5% (equivalent to a flow rate 10 μl/min). Such a periodic ripple overlaps with duration of a component peak on the chromatogram. Accordingly, it lowers sensitivity of the liquid chromatograph significantly.

Figure 6:
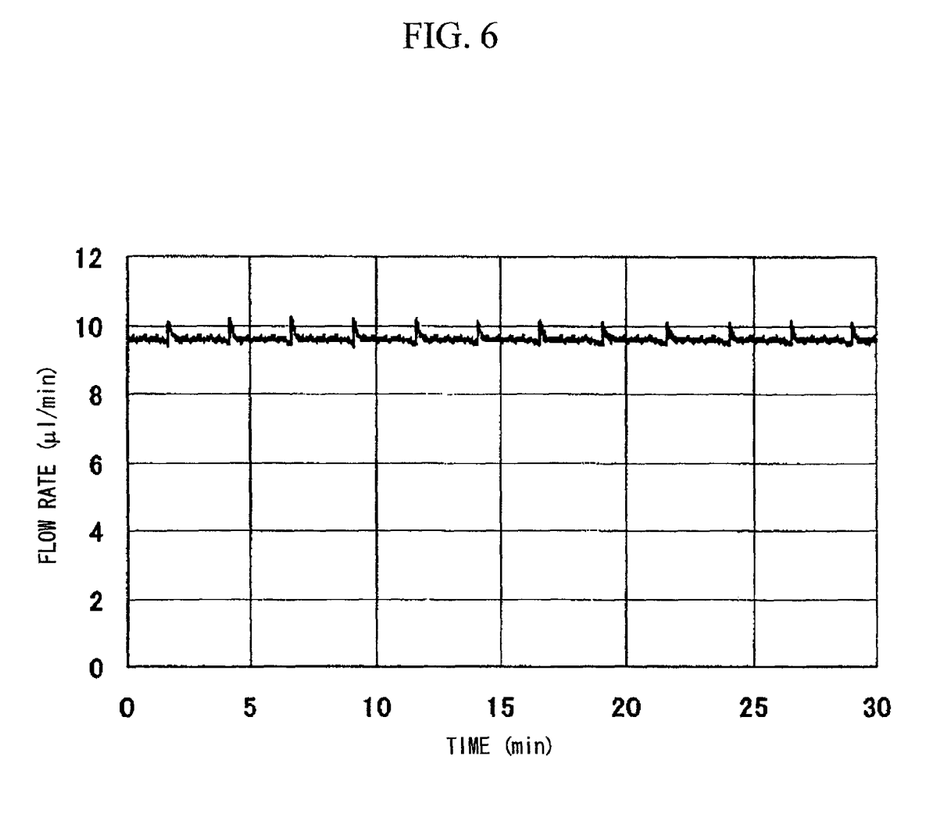
FIG. 6 is a view showing flow rate fluctuations in the high-pressure gradient liquid chromatograph using the pump device having the configuration different from that of the present invention.

FIG. 6 shows a measurement result obtained by using a flow rate sensor to measure a flow rate in a case where feeding by one of the pump units is stopped and feeding by the other pump unit is performed at a flow rate of 10 μl/min.

The flow rate sensor described above is one having the same configuration as that of the flow rate sensor used in the embodiments of the present invention, and is a mass flow sensor. The mass flow sensor includes a heater element disposed at the outside of a pipe through which a fluid flows, and temperature sensors disposed above and below the heater element. A flow rate of the fluid flowing inside the pipe causes a difference in temperature detected by the temperature sensors disposed above and below the heater element. The flow rate is detected based on the difference described above.

Specifically, the liquid mass flow sensor described above adopts principles of a thermal mass flowmeter, and has following features. Specifically, the liquid mass flow sensor is small and light, has high resistance to pressure, a low dead volume, and high responsiveness, and enables measurement without coming into contact with a liquid. Thus, the liquid mass flow sensor is suitable for being used in a liquid chromatograph apparatus.

As shown in FIG. 6, minute pulse-shaped fluctuations synchronized with a flow rate control cycle of 2.5 min are observed. The time when the flow rate fluctuations occur coincides with the end point of the double-speed control described above.

As described above, in the method using the result of detection by the two pressure sensors, unlike the present invention, errors are caused since properties of both pressure sensors do not completely coincide with each other, whereby making it difficult to eliminate the minute flow rate fluctuations.

The periodic ripple shown in FIG. 5 is the above mentioned minute flow rate fluctuations diffused inside the passage before reaching the detector and measured as an absorbance change. Moreover, the periodic ripple is an example showing how strict the accuracy and precision of the flow rate required of the pump unit are.

As described above, in the high-pressure gradient liquid chromatograph, when the flow rate in one of the two pump units fluctuates, a combined composition of mixed solvents is changed, and retention time of each component peak, and peak height and area on the chromatogram are changed. Therefore, the above changes cause uncertainty in peak identification by the liquid chromatograph apparatus, and deteriorates accuracy of quantitative measurement and reproducibility.

Meanwhile, as an embodiment of the present invention, a high-pressure gradient liquid chromatograph apparatus including the pump unit shown in FIG. 3 is formed. Moreover, evaluation is carried out under the same conditions as those in the above configuration, which is different from the present invention.

Figure 7:
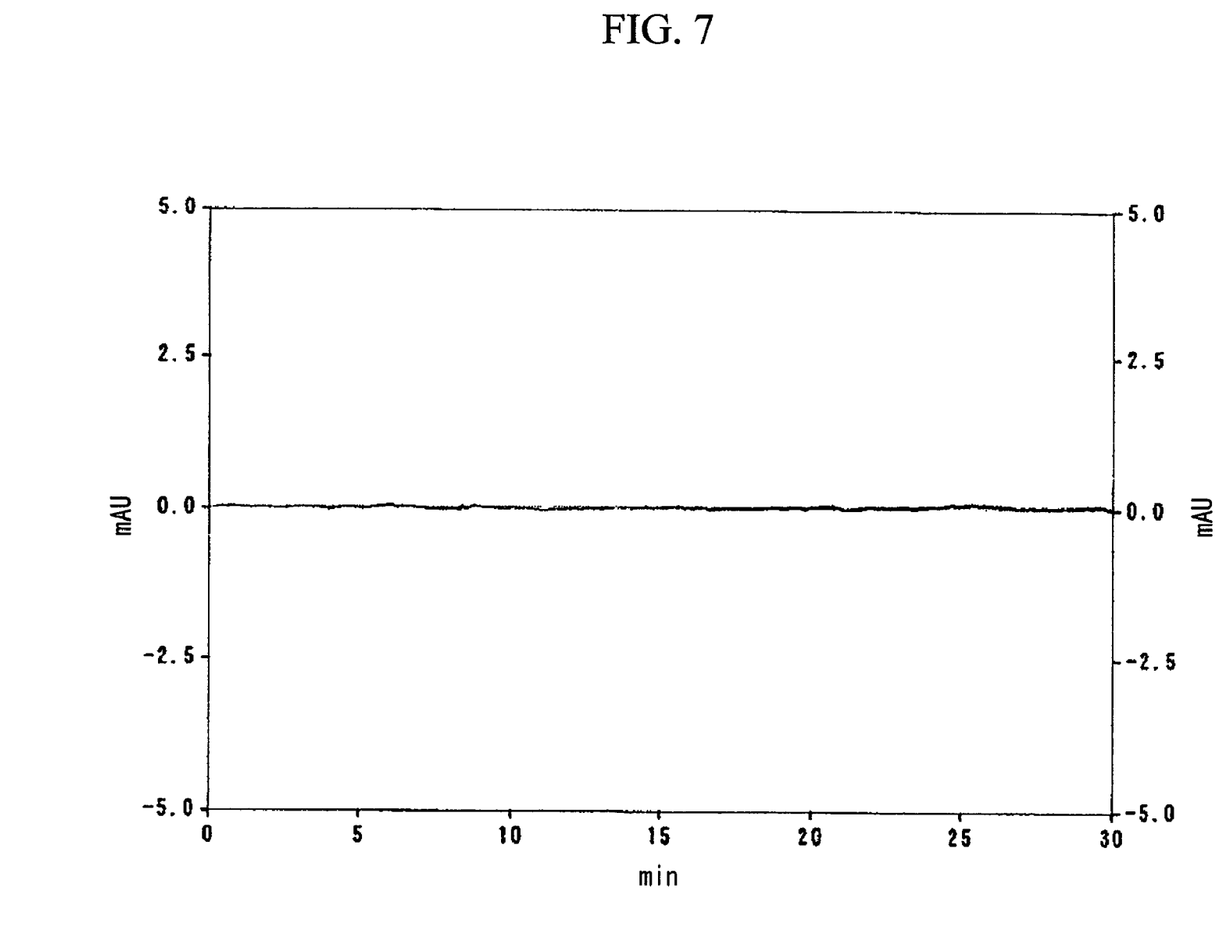
FIG. 7 is a view showing a chromatogram obtained according to the embodiment of the present invention.
Figure 8:
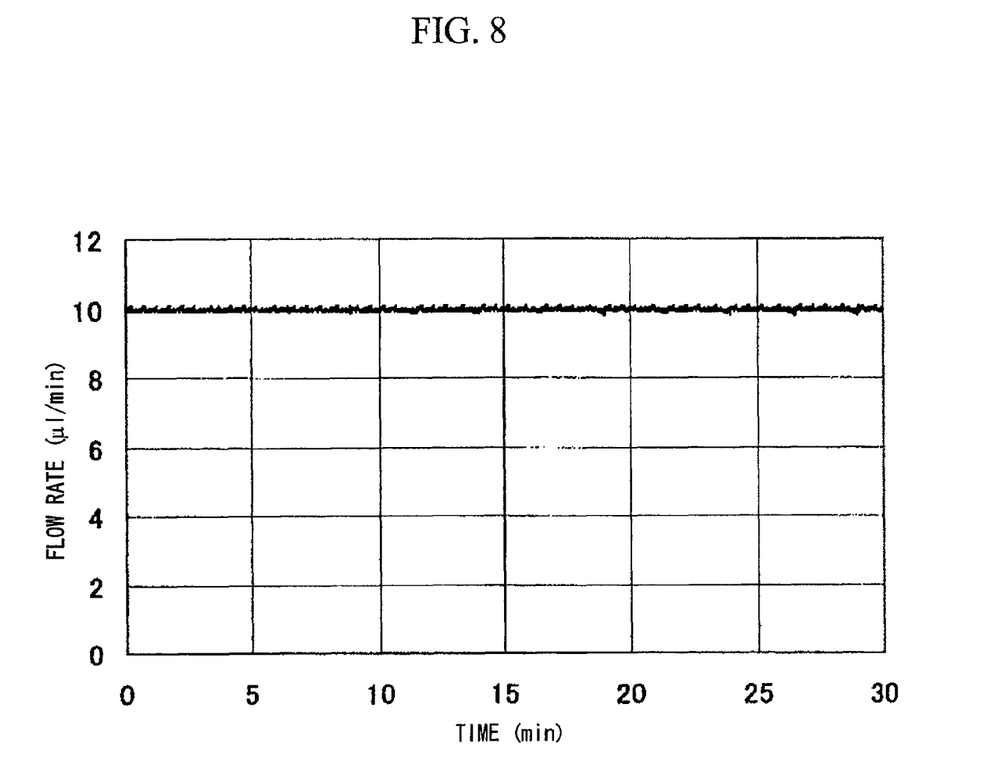
FIG. 8 is a view showing a result of evaluation of flow rate fluctuations according to the embodiment of the present invention.

FIG. 7 is a view showing a chromatogram obtained according to the embodiment of the present invention. FIG. 8 is a view showing a result of evaluation of flow rate fluctuations according to the embodiment of the present invention. The double-speed operation of the motor 12 can be returned to the original operation at the reference rotation speed by accurately detecting the moment at which the outlet side valve 6 is opened by use of the flow rate sensor 20 shown in FIG. 3. Thus, the minute pulse-shaped fluctuations synchronized with the flow rate control cycle 2, which are observed in FIG. 6, are eliminated in FIG. 8.

Furthermore, at the flow rate shown in FIG. 8, the number of revolutions of the motor 12 is controlled so as to set the flow rate detected by the flow rate sensor 10 to 10 μl/min. Thus, flow rate accuracy is also improved. As a result, the periodic ripple synchronized with the flow rate control cycle of the pump unit, which is observed in FIG. 5, is also completely eliminated in FIG. 7.

As described above, according to the configuration of the present invention, it is possible to continuously feed a solvent at an accurate flow rate and in a stable state with little flow rate fluctuation (pulsating flows). Thus, it is possible to enhance sensitivity of the liquid chromatograph apparatus, and to improve qualitative ability and reliability of quantitative results.

Figure 9:
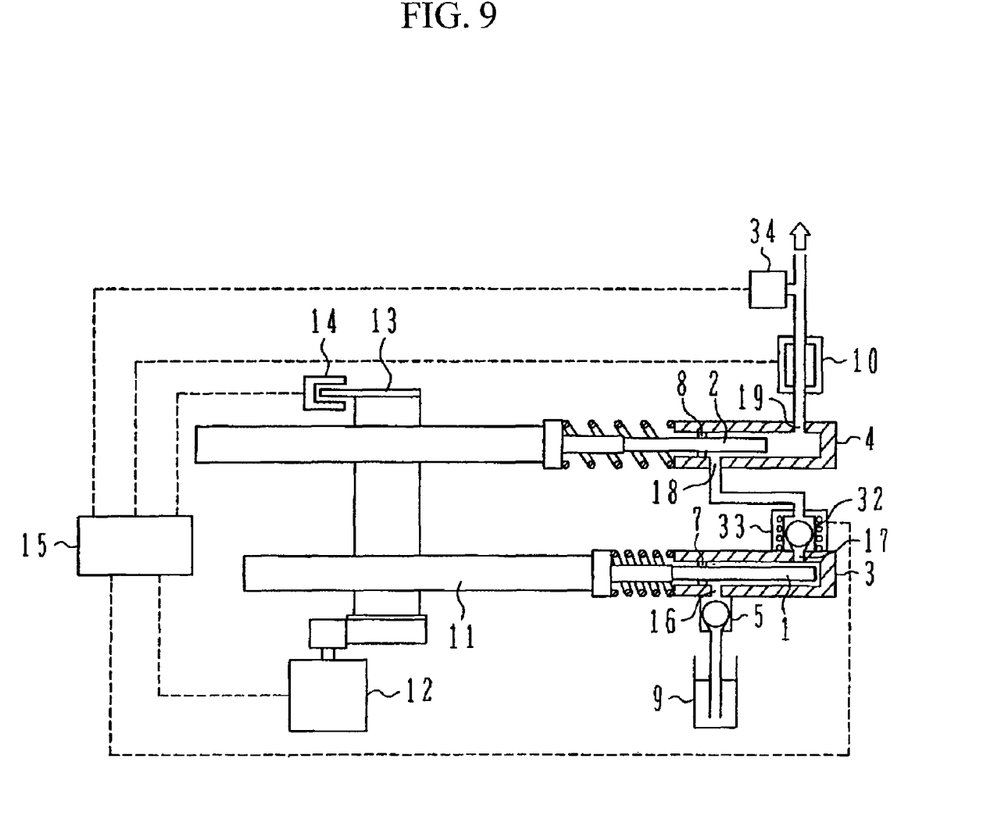
FIG. 9 is a schematic configuration diagram of a single pump unit using a check valve according to a third embodiment of the present invention.

FIG. 9 is a schematic configuration diagram of a single pump unit using a check valve according to a third embodiment of the present invention. A structural difference between the third embodiment of the present invention and the first embodiment shown in FIG. 1 is that a check valve 32 is used as the outlet side valve 6, an electromagnetic induction sensor 33 is provided to detect opening and closing states of the check valve 32, and an output signal of the electromagnetic induction sensor 33 is supplied to the controller 15. Specifically, the check valve 32 is formed of an insulating housing (preferably, polyetheretherketone or a ceramic material) which includes a magnetic ball (or a ball having a magnetic material applied thereto).

Specifically, the electromagnetic induction sensor 33 is provided, which enables the controller 15 to detect timing of the opening and the closing of the check valve 32 (up-and-down movement of the magnetic ball) without coming into contact with a liquid by detecting an induced current generated when a magnetic field in a coil is changed.

Also in the third embodiment of the present invention, the end point of the double-speed operation can be controlled by using the electromagnetic induction sensor 33, which more accurately detects the moment at which the outlet side valve 32 is opened. Thus, it is possible to achieve the same reduction in flow rate fluctuations as that in the pump unit according to the second embodiment shown in FIG. 3.

When there is a pressure difference between the first and second pump chambers 3 and 4, the outlet side valve can be opened and closed faster or slower than the movement of the pistons 1 and 2.

Therefore, in addition to movement control of the pistons 1 and 2 by use of the flow rate detected by the flow rate sensor 10, an opening and closing operation of the outlet side valve 32 is detected, and the movement control of the pistons 1 and 2 is corrected according to the opening and closing operation. Thus, precise control can be performed.

Note that, in the third embodiment of the present invention shown in FIG. 9, the flow rate sensor 10 and a pressure sensor 34 are disposed in the outlet port 19 of the second pump chamber 4. The pressure sensor 34, as described above, checks a data correlation between the system of the present invention and the conventional system, and correlation between the pressure and the flow rate, and detects occurrence of clogging inside a pipe. However, effects of the present invention can be obtained even if the pressure sensor 34 is omitted.

Moreover, in the example shown in FIG. 9, the check valve 32 and the electromagnetic induction sensor 33 are separately provided. However, the check valve 32 and the electromagnetic induction sensor 33 may be integrally provided.

Moreover, it is also possible to perform the movement control of the pistons 1 and 2 only by detecting the opening and closing operation of the check valve 32 by use of the electromagnetic induction sensor 33.

What is claimed is:

1. A liquid chromatograph apparatus comprising:
   two pump units for feeding a mobile phase;
   introduction means for introducing an object to be measured into the mobile phase fed by the pump units;
   a separation column for separating components to be measured from the object to be measured, which is introduced by the introduction means;
   detection means for detecting the components to be measured, which are separated by the separation column; and
   a data processor programmed to control operation of the two pump units, the introduction means, the separation column, and the detection means,
   wherein each pump unit includes:
   a first piston which moves back and forth in a first pump chamber having an inlet port and an outlet port,
   a second piston which moves back and forth in a second pump chamber having an inlet port and an outlet port,
   piston driving means for moving the first and second pistons back and forth,
   a position detection sensor for detecting a back-and-forth movement position of the first piston,
   a connecting pipe for connecting the outlet port of the first pump chamber to the inlet port of the second pump chamber,
   an inlet side valve, connected to the inlet port of the first pump chamber, for allowing a fluid to flow into the first pump chamber, and for checking the fluid from flowing into and out of the first pump chamber,
   an outlet side valve, that is a check valve comprising a magnetic ball and an electromagnetic induction sensor, connected to the connecting pipe, for allowing the fluid to flow into the second pump chamber from the first pump chamber through the connecting pipe, and for checking the fluid from flowing into the second pump chamber and flowing out of the first pump chamber, wherein, the electromagnetic induction sensor is connected in between the inlet port of the second pump chamber and the outlet port of the first pump chamber and detects opening and closing states of the check valve,
   a flow sensor, disposed at the outlet port of the second pump chamber, for detecting a flow rate of the fluid flowing out of the outlet port, and
   a controller programmed to control a speed of driving the first and second pistons by the piston driving means, based on the back-and-forth movement position of the first piston, which is detected by the position detection sensor, the flow rate of the fluid flowing out of the outlet port of the second pump chamber, which is detected by the flow sensor, and the opening and closing states of the check valve detected by the electromagnetic induction sensor.

2. The liquid chromatograph apparatus according to claim 1, wherein the controller controls the position detection sensor to detect that the driving means is in a first region where the fluid flows into the first pump chamber from the inlet port and the fluid flows out of the outlet port of the second pump chamber, wherein:
   the first and second pistons move at a first driving speed in the first region,
   the position detection sensor detects a start point of a second region where the first pump chamber is shifted from a fluid suction mode to a discharge mode,
   the first and second pistons move at a second driving speed when the driving means is in the second region, and when it is sensed from the flow rate of the fluid detected by the flow sensor that fluid flows only out of the second pump chamber,
   the speed of driving the first and second pistons return to the first driving speed when it is detected by the electromagnetic induction sensor that the check valve is shifted from a closing state to an opening state, and
   the second driving speed is double the first driving speed.

* * * * *